US008023102B2

(12) United States Patent
Brunner et al.

(10) Patent No.: US 8,023,102 B2
(45) Date of Patent: Sep. 20, 2011

(54) TEST METHOD FOR DETERMINING RETICLE TRANSMISSION STABILITY

(75) Inventors: Timothy A. Brunner, Ridgefield, CT (US); Colin J. Brodsky, Salt Point, NY (US); Michael B. Pike, Hopewell Junction, NY (US)

(73) Assignee: International Business Machines Corporation, Armonk, NY (US)

( * ) Notice: Subject to any disclaimer, the term of this patent is extended or adjusted under 35 U.S.C. 154(b) by 651 days.

(21) Appl. No.: 12/105,311

(22) Filed: Apr. 18, 2008

(65) Prior Publication Data

US 2009/0262317 A1      Oct. 22, 2009

(51) Int. Cl.
*G03B 27/52* (2006.01)
*G03B 27/68* (2006.01)
*G03B 27/32* (2006.01)

(52) U.S. Cl. .................. 355/30; 355/52; 355/55; 355/77
(58) Field of Classification Search .................... 355/30, 355/46, 52, 53, 55, 72, 75, 77; 430/8, 22, 430/30, 311, 312, 322; 250/492.1, 492.2, 250/492.22, 493.1; 356/432, 434, 435
See application file for complete search history.

(56) References Cited

U.S. PATENT DOCUMENTS

| | | | | | |
|---|---|---|---|---|---|
| 3,615,463 | A | * | 10/1971 | Kuschell | 430/312 |
| 4,148,065 | A | * | 4/1979 | Nakagawa et al. | 430/5 |
| 4,218,142 | A | * | 8/1980 | Kryger et al. | 356/394 |
| 4,642,276 | A | * | 2/1987 | Burtin | 430/30 |
| 5,415,952 | A | * | 5/1995 | Haruki et al. | 430/5 |
| 5,665,968 | A | * | 9/1997 | Meisburger et al. | 250/310 |
| 5,795,688 | A | * | 8/1998 | Burdorf et al. | 430/30 |
| 5,912,726 | A | * | 6/1999 | Toguchi et al. | 355/53 |
| 6,016,357 | A | * | 1/2000 | Neary et al. | 382/144 |
| 6,268,093 | B1 | * | 7/2001 | Kenan et al. | 430/30 |

(Continued)

OTHER PUBLICATIONS 157-nm Attenuated Phase-Shift Mask Materials With Irradiation Stability, Wasson, et al., Advanced Products Research & Development Laboratories, DigitaiDNA (TM) Laboratories, Motorola, Inc., Proceedings of SPIE vol. 5256 23rd Annual BACUS Symposium on Photomask Technology, pp. 199-203.

(Continued)

*Primary Examiner* — Peter B Kim
*Assistant Examiner* — Christina Riddle
(74) *Attorney, Agent, or Firm* — DeLio & Peterson, LLC; Kelly M. Nowak; Wenjie Li

(57) ABSTRACT

Methods, systems and apparatus for monitoring the state of a reticle by providing a reticle having a device exposure region in an imaging tool, defining one or more image fields across the device exposure region, and transmitting energy through the device exposure region. A detector detects the energy in the image field(s) at one or more testing intervals and a system control generates a transmission profile of average energy transmissions for each image field. Using this transmission profile, the state of the reticle is then determined at each testing interval followed by taking action based on the reticle state. The state of the reticle identifies whether the device exposure region has been deleteriously degraded, and as such, the reticle is no longer suitable for use. This is accomplished by determining if any average energy transmission of any image field across the reticle exceeds an allowable energy transmission threshold.

17 Claims, 4 Drawing Sheets

U.S. PATENT DOCUMENTS

| | | | | |
|---|---|---|---|---|
| 6,813,004 | B1* | 11/2004 | Horikoshi et al. | 355/69 |
| 6,927,003 | B2* | 8/2005 | Kim et al. | 430/5 |
| 7,251,033 | B1* | 7/2007 | Phan et al. | 356/432 |
| 2002/0012109 | A1* | 1/2002 | Suzuki et al. | 355/53 |
| 2002/0054703 | A1* | 5/2002 | Hiroi et al. | 382/149 |
| 2002/0171815 | A1* | 11/2002 | Matsuyama et al. | 355/55 |

OTHER PUBLICATIONS

Euv Mask Process Development and Integration; Guojing Zhang, et al., Intel Corporation, Santa Clara, CA; Photomask and Next-Generation Lithography Mask Technology XIII; Proceedings of SPIE vol. 6283 (2006), pp. 1-10.

* cited by examiner

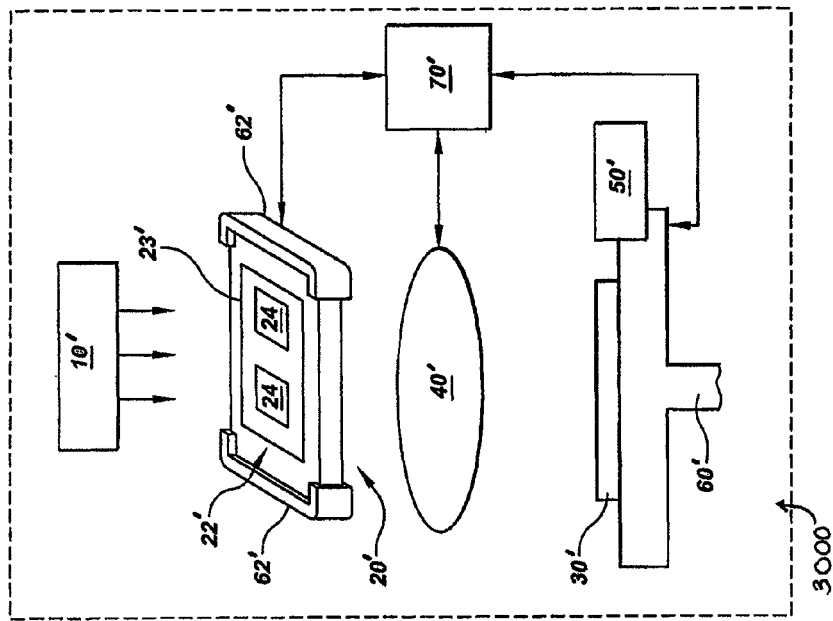
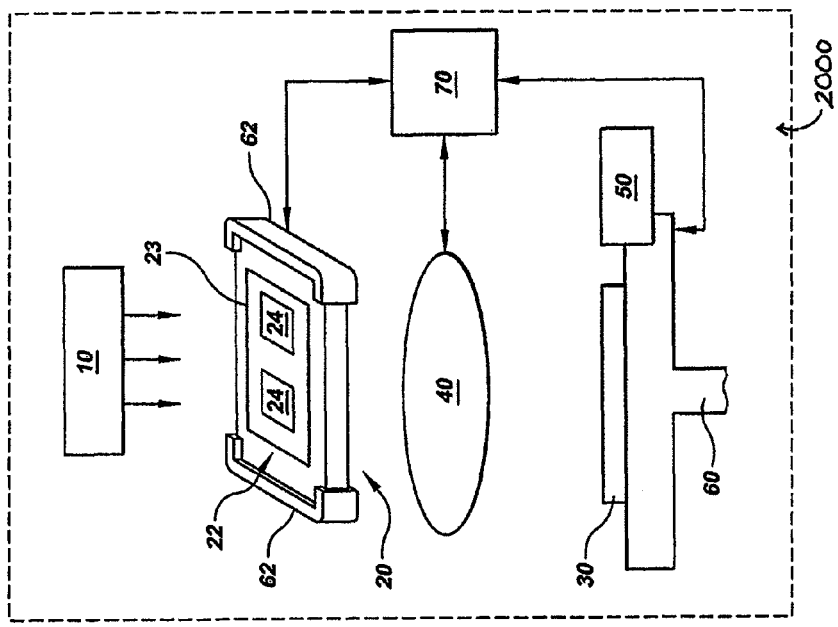
FIG. 4

TEST METHOD FOR DETERMINING RETICLE TRANSMISSION STABILITY

BACKGROUND OF THE INVENTION

1. Field of the Invention

The present invention relates generally to the manufacture of integrated circuits and, in particular, to detecting and monitoring transmission degradation of reticles used in lithographic production systems.

2. Description of Related Art

In the semiconductor industry, photolithography systems are used to transfer patterns or shapes from a reticle (i.e., photomask) to a semiconductor wafer. These patterns may be transferred a number of times across the wafer to form microelectronic circuits or other semiconductor device features.

In a typical photolithographic process, a thin layer of a photosensitive material (e.g., photo resist) is deposited over a semiconductor wafer, which may have many chips on a surface thereof. The reticle is made from a transparent plate often comprising glass, quartz, or the like. The reticle includes a device exposure region and a patterned opaque region typically comprising a chrome layer or region. The opaque pattern on the reticle represents a desired layout of a circuit or semiconductor feature.

During the photolithography process, the patterned reticle is illuminated with radiation (e.g., laser radiation or radiation from an arc lamp) in the exposure region. The reticle exposure region generally has a square or rectangular shape and is positioned in the center of the reticle. It includes both the transparent portions and opaque portions that together define the device pattern. In illuminating this exposure region, a portion of the radiation is allowed to pass through the transparent portions, while the opaque portions block another portion of the radiation. A projection lens having an image field of a given size collects the radiation that is passed through the transparent portions, and projects the reticle pattern onto the photo resist layer. This pattern creates exposed and unexposed regions on the chip(s) residing on the wafer surface, whereby the exposed regions are then removed to define the desired circuit layout on the wafer. The photolithographic process of transferring images from a patterned reticle onto a wafer may be repeated many times across the same chip on the wafer, on different chips on the wafer, or even on several chips across different lots of wafers.

In transferring the image patterns, a single patterned reticle may be repeatedly used to transfer numerous images onto the chip(s) residing across the wafer(s). However, over time and use of the reticle degradation gradually occurs to the reticle's device exposure regions. Conventional approaches aimed at solving this problem include monitoring the patterns transferred on the wafers. In these approaches any unacceptable deviations amongst the patterns transferred onto the wafer indicate that the reticle is no longer suitable for use in lithography. However, these methods are time consuming since many locations must be monitored across the wafer for detecting any such deviations. They are also costly since the deviations are not detected until the images are transferred onto the wafers, thereby leading to increased wafer scrap and decreased production yields.

Other approaches aimed at determining whether acceptable images are being transferred onto a wafer include the use of test reticles to monitor deviations, the use of metrology tools to measure and control the characteristics of the patterns formed on the wafer by adjusting the lithographic processing conditions, as well as manually inspecting both the reticle patterns and the transferred images to ensure that the transferred images are within acceptable parameters of the desired layout specifications. However, all of these approaches are time consuming, inefficient, expensive and increase scrap materials, which in turn, lead to decreased production yields.

Accordingly, a need continues to exist in the art for easily and efficiently detecting and monitoring transmission degradation of reticles used in photolithography production systems.

SUMMARY OF THE INVENTION

Bearing in mind the problems and deficiencies of the prior art, it is therefore an object of the present invention to provide methods, apparatus and systems for detecting and monitoring transmission degradation of reticles used in photolithography production systems.

Another object of the invention is to provide methods, apparatus and systems that increase production yields by detecting and monitoring reticle transmission degradation prior to wafer scrap.

It is another object of the present invention to provide methods, apparatus and systems for using a patterned reticle to its maximum yield.

A further object of the invention is to provide methods, apparatus and systems that easily, efficiently and cost effectively detect and monitor reticle transmission degradation.

Still other objects and advantages of the invention will in part be obvious and will in part be apparent from the specification.

The above and other objects, which will be apparent to those skilled in the art, are achieved in the present invention, which is directed in a first aspect to a method of monitoring the state of a reticle. The method includes providing a reticle having a device exposure region with opaque regions and transparent regions into an imaging tool. One or more image fields are defined across the device exposure region. Energy is transmitted from an energy source through the device exposure region, and is detected within the one or more image fields at a testing interval. A transmission profile of the detected energy is then generated for each image field. Using this transmission profile, a state of the reticle is determined, whereby an action is then performed based on the reticle state.

Since the device exposure region is susceptible to degradation, the present state of the reticle identifies whether or not the device exposure region has been deleteriously degraded. This degradation may include, for example, contamination or damage to the device exposure region. Further, the degradation may decrease the area of the transparent regions to decrease the amount of the energy transmitted through the device exposure region, or it may increase the area of the transparent regions, thereby increasing the amount of the energy transmitted through the device exposure region.

In this aspect of the invention, the method may further include detecting the transmitted energy within the one or more image fields at various testing intervals. Transmission profiles of the detected energy are generated for each image field across the various testing intervals, and the state of the reticle is determined based on these transmission profiles.

In determining the state of the reticle, the method may also include predefining an allowable energy transmission threshold. Average baseline energy transmissions are determined for each of the image fields. This may be calculated based on background average energy transmissions and initial average energy transmissions (i.e., prior to reticle use) at each of the one or more image fields. Once the reticle is in use, the energy transmitted through the image fields at the test intervals is detected and average energy transmissions for each of these image fields are generated at the corresponding testing interval. A transmission profile is then generated using the average energy transmissions, and the state of the reticle is determined using the transmission profile in combination with the allowable energy transmission threshold. In so doing, the transmission profile is analyzed to determine whether each of the average energy transmissions of each the one or more image fields fall within or exceeds the allowable energy transmission threshold. If all average energy transmissions fall within the allowable energy transmission threshold, then the state of the reticle identifies the reticle as being suitable for continued use. However, if any of the average energy transmissions exceeds the allowable energy transmission threshold, then the state of the reticle identifies the reticle as being no longer suitable for use.

In accordance with the invention, an action may be taken based on the state of the reticle. This action may include, but is not limited to, continuing use of the reticle, discontinuing use of the reticle, cleaning the reticle, or even replacing the reticle with a new reticle. The state of the reticle is preferably output to an end-user to provide the end-user with a quantitative measure of degradation that has occurred to the device exposure region. The opaque regions comprise an opaque material suitable for blocking the transmitted energy. Each image field preferably has a diameter ranging from about 0.1 mm to 30 mm on the wafer side. The energy source may be a radiation laser source, a radiation arc lamp source, or a light source. The imaging tool may be a lithography tool, whereby the reticle is used in lithographic processing for transferring desired patterns onto a wafer.

The methods of the invention are also directed to and may further include monitoring the equivalence of identical reticles, as well as examining different imaging tools for detecting any differences there-between based on identical reticles transferring nonequivalent images.

In other aspects, the invention is also directed to systems and program storage devices for implementing the methods of the invention.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

FIGS. 1 and 4 illustrate imaging systems in accordance with the invention for monitoring the state of a reticle.

DESCRIPTION OF THE PREFERRED EMBODIMENT(S)

Figure 2:
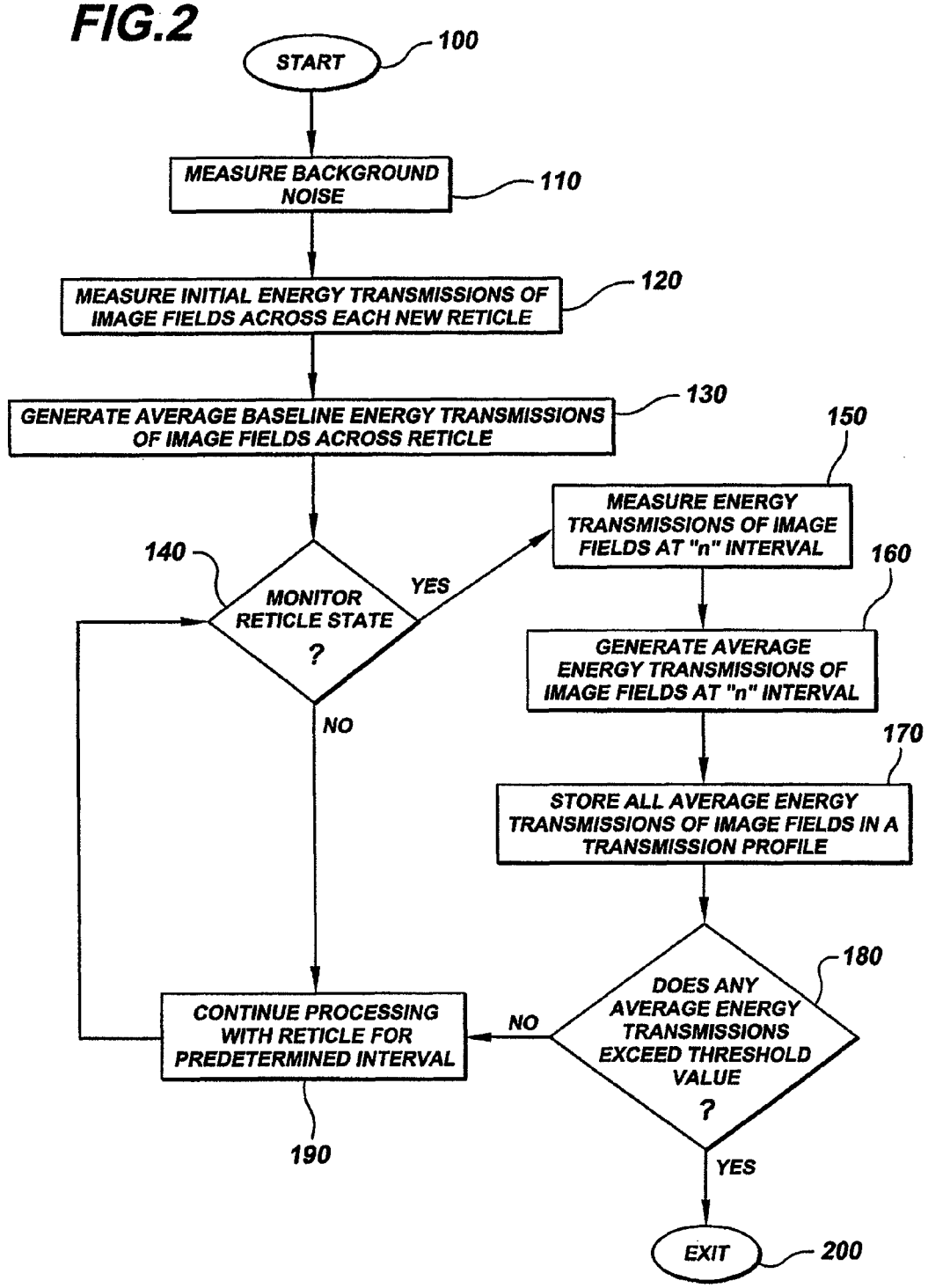
FIG. 2 illustrates a process flow for implementing the present methods of monitoring the state of a reticle.
Figure 3:
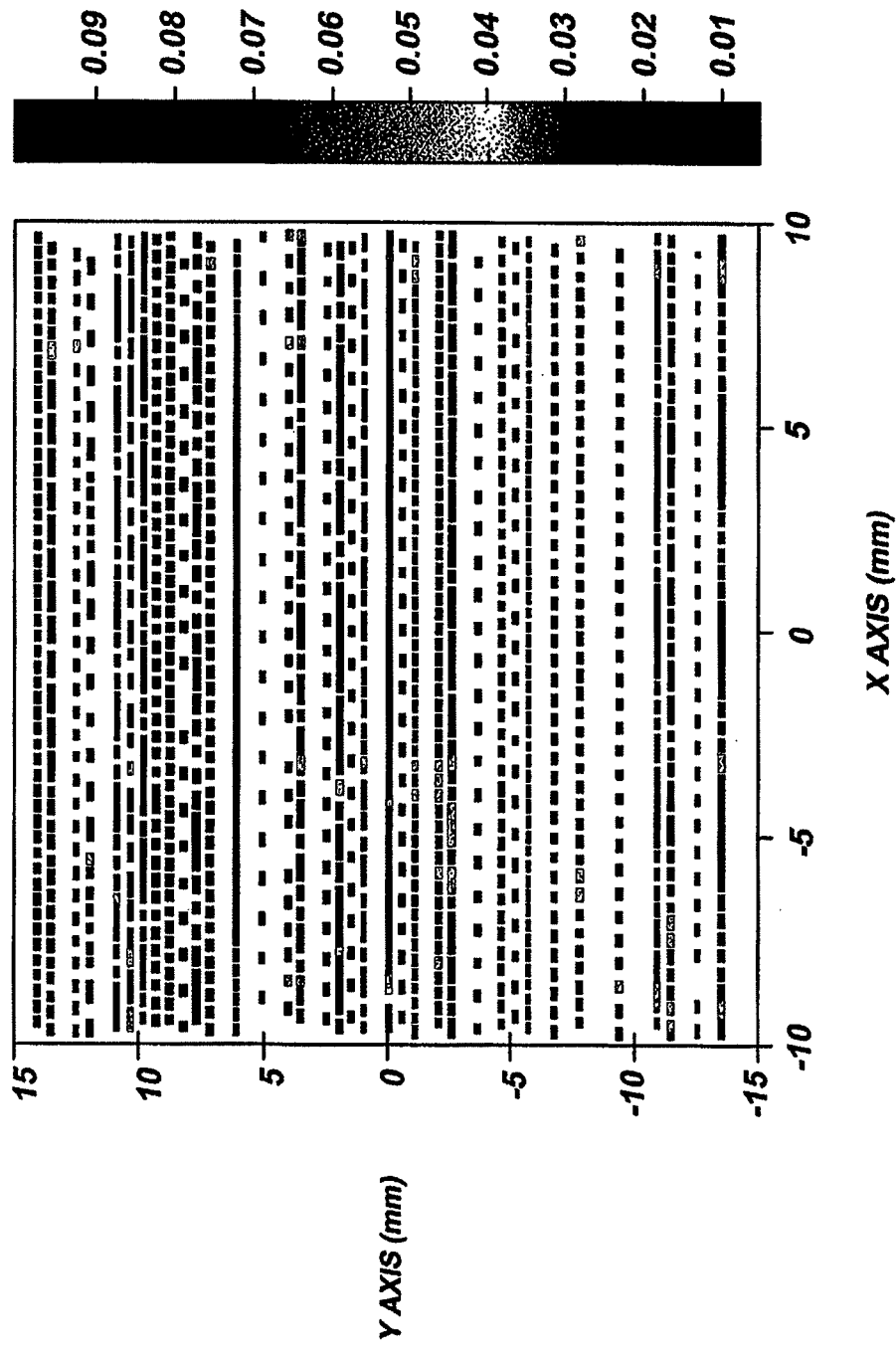
FIG. 3 illustrates a graphical display of the measured results of energy transmissions at image fields across a reticle in accordance with the invention.

In describing the preferred embodiment of the present invention, reference will be made herein to FIGS. 1-3 of the drawings in which like numerals refer to like features of the invention.

The present invention is directed to methods, apparatus and systems for detecting and monitoring photolithography reticle transmission degradation to significantly reduce product scrap, and as such, increasing production yields. The invention is suitable for use with any known imaging system. For instance, it may be used with step-and-repeat photolithography systems (i.e., steppers), which transfer exposure fields on the wafer or workpiece using a single static exposure. Alternatively, the invention may be used with step-and-scan systems (i.e., scanner), which transfer images by synchronously scanning the wafer and the mask across the lens image field.

As will be appreciated by one of skill in the art, the present invention may be embodied as methods, systems (apparatus), and/or computer program products for use in lithographic processing through implementation of a computer program or software incorporating the process steps and instructions described herein. Accordingly, the present invention may take the form of an entirely hardware embodiment, an entirely software embodiment running on general purpose hardware or an embodiment combining software and hardware aspects. Furthermore, the present invention may take the form of a computer program product on a computer-readable storage medium having computer-readable program code embodied in the medium. The computer-readable storage medium may be devised, made and used as a component of a machine utilizing optics, magnetic properties and/or electronics to perform the method steps of the present invention (e.g., an electronic design automation (EDA) tool). Any suitable computer readable medium may be utilized including hard disks, floppy disks, magnetic media such as a diskette, tapes or computer hard drive, optical media such as a CD or DVD ROM, semiconductor chips, carrier waves such as transmission over the Internet, and the like. A computer readable program code means in known source code may be employed to convert the methods described below for use on a computer.

Various aspects of the present invention are illustrated in detail in the following Figures, including flowchart illustrations and/or block diagrams. It will be understood that each block of the flowchart illustrations and/or block diagrams and/or combinations of blocks in the flowchart illustrations and/or block diagrams, can be implemented by computer program instructions. These computer program instructions may be provided to a processor or other programmable data processing apparatus to produce a machine, such that, the instructions which execute on the processor or other programmable data processing apparatus create means for implementing the functions specified in the block(s). These computer program instructions also may be stored in a computer-readable memory that can direct a processor or other programmable data processing apparatus to function in a particular manner, such that the instructions stored in the computer-readable memory produce an article of manufacture including instruction means which implement the functions specified in the flowchart and/or block diagram block or blocks.

Accordingly, blocks of the illustrations support combinations of means for performing the specified functions, combinations of steps for performing the specified functions and program instructions for performing the specified functions. It will also be understood that each block of the illustrations, and combinations of blocks in the illustrations, can be implemented by special purpose hardware.

Figure 1:
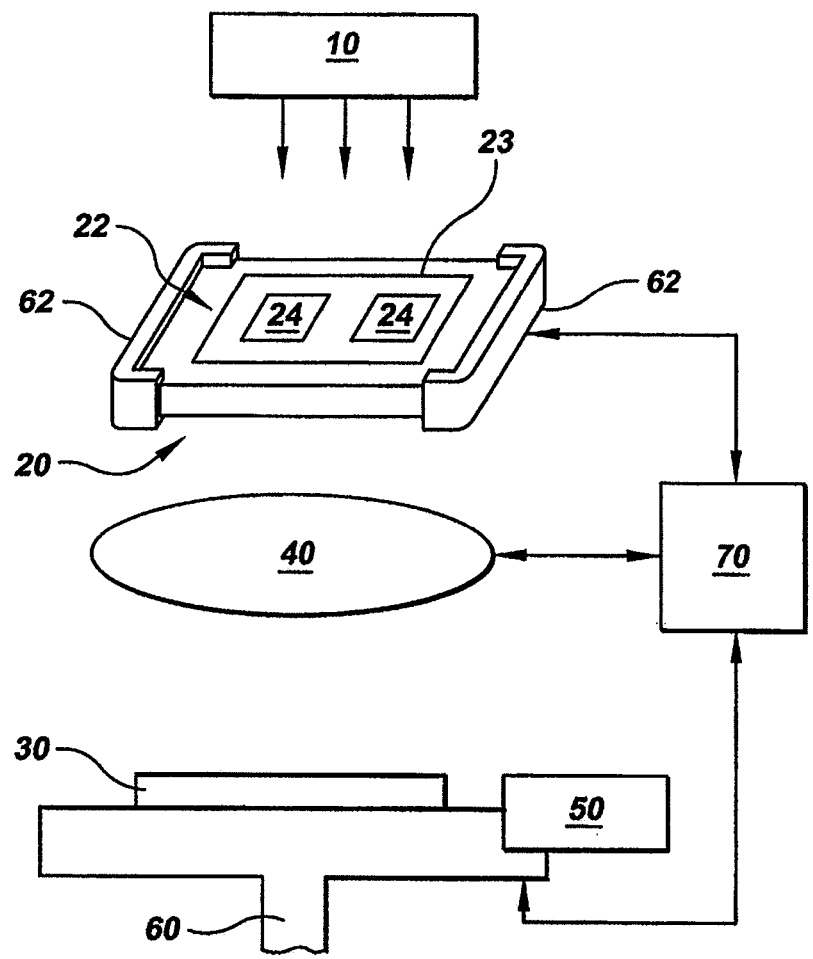

Referring now to the invention, FIG. 1 shows a lithographic system of the invention having an exposure energy source 10 for projecting exposure beams through a pattern 22 on a mask or reticle 20 (hereinafter referred to as "reticle") onto a workpiece or wafer 30 (hereinafter referred to as "wafer"). The reticle 20 may include any type of patterned plate used in lithography for transferring desired patterns onto a wafer 30, whereby the pattern in the device exposure region of such reticle is susceptible to change. The material of each reticle may include, but is not limited to, glass, quartz, and the like. Preferably, the reticle 20 resides on a movable stage 62 for aligning the reticle with at least the wafer 30, lens 40 and/or detector 50. The wafer 30 also preferably resides on a moveable wafer stage 60 for aligning the wafer with respect to the projected image of the reticle, thereby allowing the reticle to be exposed over a select region of the wafer 30.

The exposure energy source 10 may include, but is not limited to, a radiation laser source for emitting laser radiation, a radiation arc lamp for emitting radiation rays, a light source for emitting light rays, and the like. For example, the invention is particularly suitable for use with energy sources from 193 nm argon fluoride exomer lasers, 248 nm krypton fluoride exomer lasers, 13 nm extreme ultraviolet light sources or any other type of advanced lithography systems. Again, it should be appreciated that a variety of illumination or energy sources may be used to project various energy beams through the reticle onto the wafer 30.

The present invention also includes at least one lens 40 oriented between the reticle 20 and both the wafer 30 and at least one detector 50. The lens projects the energy beams emitted through the reticle onto the wafer 30 and/or detector(s) 50. One or more detectors 50 may be used to detect the amount of energy beams emitted through the transparent regions of the reticle 20. The detector(s) 50 preferably resides in the focal plane of the imaging optics, such that, it is essentially planar with a top planar surface of the wafer. That is, the top surface of the detector 50 and the top surface of the wafer reside in the same plane.

Each detector 50 is either built into the production exposure tool or is a separate, distinct component from the exposure tool. For example, the detector 50 may be built into the moveable workpiece stage 60, such that, the detector is also moveable for detecting energy transmissions at various locations across the reticle. That is, the detector may be moved into a measurement position by moving the stage 60. Alternatively, the detector may be a distinct component that is separate from the exposure tool, which is also moveable for detecting energy transmissions at various locations across the reticle. While not limiting the invention, and for ease of understanding the present invention, reference is made hereinafter to one detector; however, it should be appreciated that a plurality of detectors 50 within the optical imaging plane of the wafer may be employed.

The invention also includes a system control 70 that is connected at least to the lens 40, detector 50 and stages 60, 62. The system control component 70 controls movement of the wafer and reticle via stages 60, 62, respectively, and may optionally control movement of the lens 40 and/or the detector 50. The system control 70 receives and stores energy transmission data from the detector 50 and analyzes such data to determine whether or not the energies transmitted through the reticle meet or exceed the predefined allowable energy transmission threshold criteria.

Referring to FIG. 1, the reticle 20 has a device exposure region 22 that includes both patterned opaque regions 23 and transparent regions 24, which together represent a desired circuit layout. The opaque region 23 may comprise any type of material that has the capability of blocking the exposure beams emitted from the exposure energy source 10, thereby preventing such energy beams from contacting the wafer 30. While not meant to limit the invention, in a preferred embodiment the opaque region comprises a chrome layer.

A problem with the opaque region 23 of the device exposure region 22 is that it is susceptible to some type of instability or change capable of altering the pattern dimensions, which in turn, affects the amount of energy transmitted through the reticle. It is believed that these changes occurring to the opaque region is a result of an interaction between the radiation and the material of the opaque layer. For example, due to the repeated use and exposure of a single reticle, it has been found that the opaque regions migrate into the transparent regions 24 to increase the amount of opaque material in the transparent regions. This, in turn, decreases the amount of energy passed through the reticle, thereby affecting the image transferred onto the wafer. Alternatively, over time and use, the pattern dimensions may change by degradation of the opaque regions, which decreases the amount of opaque material on the reticle. As the areas of the opaque regions decrease, the transparent region areas increase, thereby increasing the amount of energy passed through the reticle. With any energy change passing through the reticle, whether it is an increase or decrease in energy, an undesirable affect is that the patterns transferred onto the wafer are deleteriously altered, which ultimately leads to the undesirable production of circuit patterns that do not meet the predefined circuit layout specifications.

The present invention advantageously avoids the above problem by continually monitoring any changes in energy passing through the reticle. In so doing, referring to FIG. 1 and the process flow shown in the block diagram flowchart illustration of FIG. 2, the present invention is started (Step 100). One of the initial steps of the invention is to predefine an allowable energy transmission threshold that establishes the threshold criteria/value (e.g., a limit range) for determining whether or not the device exposure region of a reticle has been deleteriously altered to a point at which the reticle is no longer suitable for use. The range of the allowable energy transmission threshold may vary in accordance with the invention, whereby it may be defined by and depend upon a number of variables including, but not limited to, the processing criteria, acceptable deviations in the end-products, use of the end-products, and the like.

This determination of whether or not the reticle meets or exceeds the predefined allowable energy transmission threshold provides an indication of the "state of the reticle" (also referred to herein as the "reticle state"). The state of the reticle represents whether or not the reticle is capable of producing acceptable product. In particular, if the transmitted energy data meets or falls within the allowable energy threshold, then the state of the reticle is such that it is suitable for use (i.e., it will produce acceptable product). However, if the transmitted energy data exceeds (does not meet or falls outside of) the allowable energy transmission threshold, then the state of the reticle is such that it is no longer suitable for producing acceptable product yields. The system control 70 outputs this reticle state data to an end-user to indicate whether or not the subject reticle is suitable for use and/or continued use. By indicating this information to an end-user before the reticle has actually exceeded the threshold criteria, the invention advantageously avoids the transfer of unacceptable images onto a wafer.

In determining the reticle state, the baseline energy transmissions emitted through the transparent regions 24 of the reticle's device exposure region are preferably determined prior to using this subject reticle. In so doing, one or more image fields that correspond to locations across the device exposure region(s) of the reticle, preferably across the transparent regions, are identified for monitoring such image fields to determine the state of the reticle over time and/or use. Wherein the image fields correspond to transparent regions, these transparent regions are preferably located substantially at the center of the reticle, as compared to the edge of the reticle. The image fields may each have a diameter ranging from about 0.1 mm to about 30 mm on the wafer side (i.e., the location where the detector is located). For a typical exposure tool, the reticle side image is 4× larger, such that, the corresponding size range for the reticle would be 0.4 mm to 120 mm.

Once the one or more image fields have been pre-determined, any background noise is then measured (Step 110). Without the reticle being in position on stage 62, the detector 50 is moveably positioned under stage 62 to the one or more pre-determined image fields. The detector, reticle stage, lens and/or energy source may be moved to detect and measure the energies transmitted from the energy source 10 within each of the various pre-determined image fields (i.e., pre-determined locations).

In measuring these image fields, a single detector 50 may be used and sequentially moved to all or a select few of the various pre-determined image fields for detecting the transmitted energies at each such location. For instance, wherein the subject reticle has a 10×10 matrix and the detector has a 1,000 micron square area, the detector may be accurately moved to a number of the different image fields (e.g., 100 image fields) across this 10×10 matrix within a very short time frame (e.g., from about 10 seconds to about 3 minutes, preferably less than 1 minute) for detecting the energy transmissions at all of these various image field locations.

Alternatively, a number of different detectors 50 may be used for simultaneously or sequentially detecting the energy transmissions at each of these various image field locations. In this aspect, the plurality of detectors 50 may be set to measure energy transmissions at one location, or they may be programmed to move to various locations under the reticle that correspond to transparent regions for obtaining the energy transmissions at each of such locations. As another alternative, rather than using a plurality of different detectors, a split detector may be employed for simultaneously obtaining energy transmissions at these locations. Still further, camera type array of detectors may be used to capture the entire image of the reticle.

Again, without the reticle being in position, the detector 50 obtains the energy transmissions at the various pre-determined image fields. These energy measurements represent background energies (i.e., background noise) that may interfere with downstream energy transmissions over time and use of the subject reticle, and are necessary for obtaining baseline energy transmissions across the subject reticle 20 prior to use. The background energy transmissions that are detected within the various image fields are then transferred from the detector 50 to the system control 70 for generating a background average energy transmission for each of the various measured pre-determined image fields, which is stored in the system control 70 for determining the state of the reticle.

Once the background average energy transmissions are obtained, the subject reticle 20 is provided within the present lithography system. This reticle 20 may be a new reticle, test reticle or even a reworked reticle. The reticle has a predetermined patterned device exposure region(s) 22 that is to be used for transferring patterns onto a wafer. However, prior to using this reticle, the initial energy transmissions emitted through the transparent regions 24 are detected and measured using the detector 50 (Step 120).

In so doing, any combination of the detector, reticle stage, lens and/or energy source are moved to the various previously measured pre-determined image fields that correspond to locations of the device exposure regions 22, preferably to the transparent regions 24. With the detector positioned within the optical imaging plane of the wafer at these various pre-determined image fields, the detector measures the energies transmitted from the energy source 10 through the transparent regions 24 of the reticle. These initial energies include the actual energies transmitted through the reticle in combination with the background energies. Preferably, the initial average energy transmissions are obtained every time a new reticle is loaded into the process tool prior to use in lithographic processing.

The detector 50 transfers these initial energy transmissions measured across the reticle to the system control 70, which generates a number of initial average energy transmissions across the reticle corresponding to the various image fields. Since the average energies transmitted through the reticle prior to use include both the actual reticle energies and the background energies, the system control 70 subtracts the background average energy transmissions from the initial average energy transmissions at corresponding image fields to generate the reticle's actual average baseline energy transmissions for each of the various image fields prior to using the reticle (Step 130). These actual average energy transmissions for each predetermined image field across the reticle are stored in a database in the system control 70 for comparison with previous and future transmission measurements. For example, the actual average energy transmissions may be stored in a log file in the system control.

After these initial actual average energy transmissions are obtained for the subject reticle, the reticle is then used to pattern a wafer or number of wafers. Since degradation of the reticle pattern occurs over time and use, the average energy transmissions at the various previously measured pre-determined image fields across the reticle are re-measured at testing intervals. These testing intervals may be automatic set test intervals that include, for example, lot intervals, wafer intervals, time intervals and the like. For instance, the previously measured transmission locations may be measured for current average energy transmission data every "L" lots of processed wafers (e.g., "L" equals every 10 lots), every "W" wafers (e.g., "W" equals every 500 wafers), or even every "T" seconds, minutes or hours.

Thus, the present process flow then determines whether or not it is time to monitor the state of the reticle (Step 140). If it is not time to test the reticle state, the process flow continues using the reticle (Step 190) and repeats the testing time of whether or not it is time to monitor the state of the reticle. This can be done either manually be an end-user or atomically by the present system at a set interval or time point (e.g., at the "n" interval).

However, in Step 140 if it is determined that it is time to monitor the state of the reticle (e.g., the process flow is at the "n" interval), then the process continues to check the state of the reticle by measuring the energy transmissions of the image fields at this "n" interval (Step 150). The detector 50 is repositioned in the optical imaging plane of the wafer for in-situ testing of the reticle during the tool and production run times. As described above, the detector is movably positioned to measure the energy transmissions through the reticle, preferably through the transparent regions 24, at the various pre-determined image fields across the reticle so that substantially the same areas of the reticle are tested each time (e.g., preferably to about within 1 micron accuracy). These measured first testing interval energy transmissions of the image fields are transferred from the detector 50 to the system control 70 for generating average energies of each image field at this first testing interval (e.g., by subtracting any background average energies from the measured first testing interval energies) (Step 160).

The system control 70 stores all testing interval average energy transmissions for comparison with previous and future transmission measurements (Step 170). The invention then continues by determining whether or not any stored average energy transmission exceeds the threshold criteria or values (Step 180). This is accomplished by comparing currently measured testing interval average energies with previous average energy transmissions. If any currently measured testing interval average energy exceeds the threshold criteria, then the reticle is no longer suitable for use and the present process is exited (Step 200). At this point a new reticle may be loaded and the present process flow repeated. However, if all of the currently measured testing interval average energies fall within the threshold criteria, then the process continues using the subject reticle (Step 190) until it is time to determine whether or not the reticle state should be monitored (Step 140).

For instance, at the first testing interval for a subject reticle, in the step of determining whether or not any stored average energy transmission exceeds the threshold criteria or values (Step 180), the system control 70 may compare the stored first testing interval average energies against the initial actual average energies of the same image fields to determine the state of the reticle. If the average amount of energy passed through the image fields across the reticle at the first testing interval falls within a predefined allowable energy transmission threshold, then the reticle is suitable for continued use (go to Step 190). However, if the average amount of energy passed through the image fields falls outside of the allowable energy transmission threshold range, then the reticle is no longer suitable for use (so to Step 200).

While not meant to be limiting, as another example of the invention the predefined range of the allowable energy transmission threshold may be pre-set to a 3% deviation from a targeted value that is represented by the initial average energies of each image field prior to use of the reticle. Any subsequently performed interval transmission measurements, within any of the image fields, having an average energy transmission greater than a 3% deviation from target, whether it is above target or below target, indicates that the transparent and/or opaque regions of the reticle's device exposure regions have been deleteriously compromised or damaged (e.g., contaminated), potentially to a point at which the reticle is no longer suitable for use. This contamination of the device exposure regions may cause either an increase or decrease in the amount of energy transmitted through the device exposure region of the reticle. Even if only a single or a few of the image fields across the reticle show damage to a single or few locations of any device exposure region, the reticle may be considered compromised and no longer suitable for use. At this point the reticle may be removed and replaced with another reticle.

However, during the interval testing, if it is found that subsequently performed interval measurements fall within the allowable energy threshold ranges, then the reticle is suitable for continued use (Step 190). The energy transmissions across the reticle will then continue to be monitored (Step 140), preferably automatically monitored at the preset periodic intervals until it is found that the reticle is no longer usable (e.g., it is damaged, contaminated, etc.). Alternatively, the energy transmissions across the reticle may be manually monitored by manually interrupting the present process flow, and then either continuing the present process flow if it is found the reticle is viable for use or exiting the process flow and discontinuing use of such reticle. Since the testing is performed in-situ during the lithography processing run time, and due to the speed and repeatable accuracy of positioning of the components of the invention, each reticle testing interval can be accomplished rapidly, for example, within about 1 to about 3 minutes, or more preferably within less than 1 minute.

The above interval testing is preferably automatically repeated at the preset intervals, whereby at each test interval the results of the measured energy transmissions across each predetermined image field are transferred to the system control 70 (Step 150). The system control 70 generates average energy transmissions at each test interval for all measured image fields and stores such average energy transmissions of each test interval (Step 160). The system control 70 also generates and stores a transmission profile or map of the average transmission energies over time for each image field (Step 170). Again, these image fields corresponding to the transparent and/or opaque regions of the reticle's device exposure regions. The system control 70 uses the transmission profiles to compare average energy transmissions of each image field against their corresponding previously measured interval energies, preferably against the initial average energies, to determine the state of the reticle (Step 180). In so doing, if it is determined at one of these test intervals that any average energy transmission of any image field exceeds the allowable energy transmission threshold, then the reticle state at this test interval is identified as being no longer suitable for use, and the process is exited (Step 200).

The system control 70 outputs all reticle state data to end-users of the invention to indicate whether or not the subject reticle being employed is suitable for use. Included within the output transmitted to an end-user may be a graphical display of the reticle transmission data at the various image fields across the reticle that is in use. FIG. 3 illustrates an example of such a graphical display of the spots or measured image fields across the reticle transmission data using a 193 nm exposure tool at a 4× reduction system. The system control uses this data to generate the average energy transmission intensities across each image field and stores such results, preferably in a transmission profile for later use.

By outputting the transmission data, and in particular the reticle state data, the invention enables the end-user to monitor the transmission state of the reticle as it degrades and, as such, advantageously allows the end-user to take action before the reticle transfers unacceptable images onto the wafer. For instance, since the end-user is able to closely monitor the reticle degradation as it occurs, the end-user is provided with ample time to supply (e.g., order) and load a new reticle into the processing equipment prior to the currently used reticle degrading below the allowable energy threshold. Accordingly, a user of the invention can advantageously monitor a reticle during use, and determine whether or not the reticle is transferring acceptable or unacceptable images onto the wafer, thereby providing the end-user with the ability of avoiding the transfer of unacceptable images onto the wafer. The foregoing steps of the invention are repeated for every new reticle provided within a lithography processing tool.

As an example of the invention, two identical reticles for use in lithographic processing are shown in the below Table 1. These reticles have been predefined with an allowable energy transmission threshold of 8% deviation from target. The two identical reticles are processed in accordance with the invention in first and second runs on the lithography tool. Prior to using the reticles, the baseline average energy transmissions of the image fields are determined across the reticles, and are referred to as having a "clean" reticle state in the table below. At the "n" testing interval, the energy transmissions across the same energy fields are re-measured, and the average energy transmissions of the image fields at the "n" interval are generated and stored. The average energy transmissions at the "n" interval are referred to as having a "dirty" reticle state in the table below. Results of at least one image field from the two runs are shown in Table 1:

TABLE 1

| Run # | Reticle State | Average Reticle Transmission | Loss in Reticle Transmission |
|---|---|---|---|
| 1 | Clean | 1.25% | |
| 1 | Dirty | 1.19% | 5% loss |
| 2 | Clean | 1.31% | |
| 2 | Dirty | 1.18% | 11% loss |

Wherein the target value for the first run is the average energy transmission at the clean reticle state (i.e., prior to use), the loss in transmission from the clean to the dirty reticle states in this first run is about a 5% deviation loss. In the second run, with the target value being the average energy transmission at the clean reticle state at the start of this second run, the loss in transmission from the clean to the dirty reticle states about an 11% deviation loss. Since the acceptable transmission threshold is an 8% deviation from target, only the reticle of the first run is suitable for continued use. The reticle of the second run has been compromised (e.g., damaged, contaminated, etc.), and as such, is no longer suitable for use. Further, knowing that the first run reticle has a 5% loss in reticle transmission, the end-user can monitor any gradual degradation of this reticle at future testing intervals, and if found to be too close to the allowable threshold value, the end-user can remove the reticle before it undesirably transfers unacceptable images on the wafer.

It has been found that reticle transmission degradation may be a result of a number of different factors depending upon the type of reticle, as well as the material of the opaque regions. However, a common feature is that the pattern on each of these reticles is susceptible to some type of instability or change that is capable of altering the pattern dimensions, thereby undesirably affecting the amount of energy transmitted through the reticle. Over time and use, these changes in the pattern dimensions affect the images transferred onto the wafer, such that, these transferred patterns begin to differ from the desired circuit layout.

While not meant to be limiting, the present invention is particularly useful for reticles having chrome opaque regions. Over time and use of such reticles, it is believed that the energy source's energy (i.e., heat or radiant energy) causes a reaction at the opaque layer, perhaps even chemically reacting with such opaque layer, to chemically alter the chrome layer to chrome oxide. These changes are especially exhibited at the visible and UV lights. This reaction also causes the chrome oxide, also referred to as "Crud", to undesirably migrate into the transparent regions. The Crud migrates onto the reticle pattern sidewalls, thereby altering the pattern of the device exposure region. In particular, the Crud growth decreases the area of the transparent regions to decrease the amount of energy transmitted through the reticle, which in turn, deleteriously affects the pattern transferred onto the wafer. Thus, an end-user of the invention is advantageously provided with the capability of monitoring the state of the reticle by detecting any early Crud growth, and monitoring this Crud growth simultaneously at a plurality of sites across the reticle. By monitoring the Crud growth, the user is able to closely observe the degradation of the reticle and predicting when the reticle will no longer be usable, before such reticle is actually unusable, thereby avoiding transferring of any undesirable or defective images onto the wafer.

Accordingly, the present invention advantageously provides an end-user with a quantitative measure of any degradation (e.g., damage or contamination) that has occurred to the device exposure region of a reticle over time and/or use. This, in turn, allows the end-user to determine whether or not to react to such problem, such as, by replacing the reticle if to much degradation is present, or even trying to remove any degradation (e.g., contamination) from the subject reticle and re-using the cleaned reticle. Thus, the present invention provides an efficient, timely and low cost approach for monitoring the state of the reticle.

Further, in accordance with the foregoing description, referring to FIG. 4 it will be appreciated and understood that the present invention may also be used to monitor the state and equivalence of identical reticles. In semiconductor fabrication, several identical reticles 20 and 20' are often simultaneously used on various lithography tools 2000, 3000 to produce high volume product yields. The present methods, systems and program products may be used to detect any reticle-to-reticle variations amongst identical reticles 20, 20'. In so doing, an allowable transmission variance threshold is defined for the identical reticles to establish the criteria at which these identical reticles will transfer substantially equivalent images, and in turn, produce substantially equivalent product yields. That is, the allowable transmission variance threshold is used to determine whether or not any corresponding image fields at corresponding time intervals amongst any of the identical reticles varies too significantly from the other identical reticles. This is accomplished by monitoring the image fields of the identical reticles, followed by comparing the average energy transmissions of corresponding image fields at corresponding time intervals for these identical reticles. If any of such average energy transmissions exceeds the allowable transmission variance threshold, then it is indicated that such reticle is no longer suitable for use since it will yield products that substantially differ from the product yields of the other identical reticles. Of course, if all average energy transmissions fall within the allowable transmission variance threshold, then the identical reticles will produce substantially equivalent product yields.

Also referring to FIG. 4 the invention may be used to detect any differences from exposure tool 2000 to exposure tool 3000. In this aspect, each exposure tool is to transmit and measure substantially equivalent energy transmissions for producing equivalent product yields. The present invention may be used to confirm consistency across the exposure tools using predefined threshold criteria, whereby if any of the tools exceed the predefined threshold criteria at the present set measuring intervals, then an indication is provided that an error exists with such tool(s). The end-user can then stop the present process, and correct the error with the exposure tool. In this aspect, the invention beneficially reduces reticle contamination by improving control of the exposure tools.

While the present invention has been particularly described, in conjunction with a specific preferred embodiment, it is evident that many alternatives, modifications, and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A method of monitoring the state of a reticle comprising:
providing a first reticle having a first device exposure region with opaque regions and transparent regions;

providing said first reticle in a first imaging tool;
defining one or more image fields across said first device exposure region;
providing a second reticle having a second device exposure region, said first and second reticles being identical reticles;
defining an allowable transmission variance threshold for said first and second reticles, said allowable transmission variance threshold identifying whether said first and second reticles will transfer substantially equivalent images;
providing said second reticle in a second imaging tool;
defining said one or more image fields across said second device exposure region of said second reticle;
transmitting a first energy from a first energy source through said first device exposure region of said first reticle;
transmitting a second energy from a second energy source through said second device exposure region of said second reticle;
detecting in each of said first and second imaging tools said first and second transmitted energies within said one or more image fields across said first and second reticles at a testing interval;
generating transmission profiles of each of said first and second detected energies for said one or more image fields across said first and second reticles;
determining a state of each said first and second reticle based on said first and second transmission profiles;
monitoring equivalence of said identical first and second reticles by comparing each of said first transmission profile of said first reticle and said second transmission profile of said second reticle with said allowable transmission variance threshold to determine whether said first and second reticles will transfer substantially equivalent images; and
performing an action based on said state of each said reticle.

2. The method of claim 1 wherein said step of detecting each of said first and second imaging tools is performed using one or more detectors, said one or more detectors comprises a single moveable detector, said single moveable detector being moved to said number of different image fields across said device exposure region for detecting said transmitted energy with each of said number of different image fields.

3. The method of claim 1 wherein each said device exposure region is susceptible to degradation comprising contamination of said device exposure region.

4. The method of claim 1 wherein each said device exposure region is susceptible to degradation comprising damage to said device exposure region.

5. The method of claim 1 wherein each said device exposure region is susceptible to degradation of each said device exposure region that results in a decrease in area of said transparent regions, thereby decreasing the amount of said energy transmitted through each said device exposure region.

6. The method of claim 1 wherein each said device exposure region is susceptible to degradation of each said device exposure region that results in an increase in area of said transparent regions, thereby increasing the amount of said energy transmitted through each said device exposure region.

7. The method of claim 1 wherein said step of detecting each of said first and second imaging tools is performed using one or more detectors, said one or more detectors comprises a plurality of detectors, said plurality of detectors detecting said transmitted energy within said number of different image fields.

8. The method of claim 1 wherein said method steps further comprise:
predefining said allowable transmission variance threshold for said first and second reticles;
determining average baseline energy transmissions for each of said number of different image fields;
detecting said transmitted energy within said number of different image fields at said testing interval;
generating average energy transmissions of each of said number of different image fields at said testing interval;
generating said number of transmission profiles using said average energy transmissions; and
determining said state of each said reticle using said transmission profiles by comparing said average energy transmissions of each of said number of different image fields to their corresponding said average baseline energy transmissions to determine if any of said average energy transmissions of said number of different image fields fall outside of an allowable energy transmission threshold range.

9. The method of claim 8 wherein said step of determining said average baseline energy transmissions comprises:
prior to providing each said reticle within said first and second imaging tool, measuring background noise and generating background average energy transmissions at each of said number of different image fields;
providing each said reticle within said first and second imaging tools;
transmitting said first and second energy from said first and second energy source through said device exposure regions;
measuring initial energy transmissions within said number of different image fields;
generating initial average energy transmissions for each of said number of different image fields; and
calculating said average baseline energy transmissions using said background average energy transmissions and said average energy transmissions for each of said number of different image fields.

10. The method of claim 8 wherein said step of determining said state of said reticle comprises:
determining said state of each said reticle wherein,
if all average energy transmissions of said number of different image fields fall within said allowable energy transmission threshold range, then said state of said reticle identifies said reticle as being suitable for continued use,
if any of said average energy transmissions of said number of different image fields exceed said allowable energy transmission threshold range, then said state of said reticle identifies said reticle as being no longer suitable for use.

11. The method of claim 1 wherein said action is selected from the group consisting of continuing use of said reticle, discontinuing use of said reticle, cleaning said reticle, and replacing said reticle with a new reticle.

12. The method of claim 1 wherein said opaque regions comprise an opaque material suitable for blocking said transmitted energy.

13. The method of claim 1 wherein each of said one or more image fields has a diameter ranging from about 0.1 mm to about 30 mm.

14. The method of claim 1 wherein each said energy source is selected from the group consisting of a radiation laser source, a radiation arc lamp source, and a light source.

15. The method of claim 1 wherein each said imaging tool comprises a lithography tool and said reticles are used in lithographic processing for transferring desired patterns onto a wafer.

16. The method of claim 1 further including outputting said state of each said reticle to an end-user to provide said end-user with a quantitative measure of degradation that has occurred to each said device exposure region.

17. The method of claim 1 wherein if it is determined that said first and second reticles transfer nonequivalent images, then said method further including the step of examining said first imaging tool and said second imaging tool for detecting any differences there-between.

\* \* \* \* \*